United States Patent
Gansen et al.

(10) Patent No.: US 8,657,986 B2
(45) Date of Patent: Feb. 25, 2014

(54) POLYURETHANE PLASTER FOR THE TRANSDERMAL APPLICATION OF ACTIVE SUBSTANCES, AND METHOD FOR THE PRODUCTION THEREOF

(75) Inventors: Peter Gansen, Seeburg (DE); Michael Dittgen, Apolda (DE); Ingeborg Steinfatt-Hoffmann, Hoerden (DE); Christian Schulte, Goettingen (DE); Juergen Henze, Duderstadt (DE)

(73) Assignee: Otto Bock PUR LifeScience GmbH, Duderstadt (DE)

( * ) Notice: Subject to any disclaimer, the term of this patent is extended or adjusted under 35 U.S.C. 154(b) by 177 days.

(21) Appl. No.: 13/131,381

(22) PCT Filed: Nov. 26, 2009

(86) PCT No.: PCT/EP2009/008432
§ 371 (c)(1),
(2), (4) Date: May 26, 2011

(87) PCT Pub. No.: WO2010/060621
PCT Pub. Date: Jun. 3, 2010

(65) Prior Publication Data
US 2011/0229677 A1 Sep. 22, 2011

(30) Foreign Application Priority Data
Nov. 26, 2008 (DE) .......... 10 2008 059 054

(51) Int. Cl.
*B29C 65/52* (2006.01)
*B32B 37/00* (2006.01)
*B32B 38/04* (2006.01)
*B32B 38/10* (2006.01)
*B32B 43/00* (2006.01)
*C09J 5/00* (2006.01)

(52) U.S. Cl.
USPC ..... 156/249; 156/250; 156/307.3; 156/307.7; 156/719

(58) Field of Classification Search
USPC ........ 156/247, 249, 250, 307.1, 307.3, 307.5, 156/307.7, 701, 719; 602/54, 57, 900; 206/440
See application file for complete search history.

(56) References Cited

U.S. PATENT DOCUMENTS

| | | | |
|---|---|---|---|
| 5,686,098 A | 11/1997 | Murphy | |
| 6,149,614 A * | 11/2000 | Dunshee et al. | 602/57 |
| 6,824,885 B2 * | 11/2004 | Fitch et al. | 428/483 |
| 7,994,381 B2 * | 8/2011 | Baron et al. | 602/41 |
| 2009/0181250 A1 * | 7/2009 | Zmarsly et al. | 428/352 |

FOREIGN PATENT DOCUMENTS

| | | |
|---|---|---|
| DE | 195 26 864 | 1/1997 |
| DE | 197 38 855 | 3/1999 |

(Continued)

*Primary Examiner* — Sing P Chan
(74) *Attorney, Agent, or Firm* — Whitham Curtis Christofferson & Cook, PC

(57) ABSTRACT

A method for producing an active substance-containing polyurethane plaster for transdermal application is described, said plaster containing at least one active substance at a highly accurate declared dose. In the described method, a solvent-free active substance-containing polyurethane is produced by reactively coating a solvent-free active substance-containing polyurethane material (40), which is mixed in a coating unit (60) immediately before or during the application process, onto an elastic backing foil (20) that has been rendered non-extensible at least in the direction in which the applied polyurethane material is processed by means of a supporting, adhering auxiliary foil (30) which is at least mono-axially non-extensible.

12 Claims, 4 Drawing Sheets

(56) References Cited

FOREIGN PATENT DOCUMENTS

| | | |
|---|---|---|
| DE | 100 47 700 | 4/2002 |
| DE | 101 28 685 | 12/2002 |
| DE | 103 60 592 | 7/2005 |
| EP | 1 190 723 | 3/2002 |
| EP | 1 249 480 | 10/2002 |
| EP | 1 438 943 | 7/2004 |
| EP | 1 815 875 | 8/2007 |
| WO | WO 93/10772 | 6/1993 |
| WO | WO 01/39752 | 6/2001 |

\* cited by examiner

Fig. 5  Higuchi plot for scopolamine release from TP-1, TP-2 and TP-C

Higuchi plot for testosterone (Tst) release from TP-ICO to TP-400, Intrinsica and Testopatch

POLYURETHANE PLASTER FOR THE TRANSDERMAL APPLICATION OF ACTIVE SUBSTANCES, AND METHOD FOR THE PRODUCTION THEREOF

FIELD OF THE INVENTION

The invention relates to a polyurethane patch for the transdermal application of active ingredients, and to a method for producing an active ingredient-containing polyurethane patch of this kind by reactive coating of a support.

BACKROUND

In the prior art there are various known, therapeutically useful transdermal patches where solvent-containing polymer mixtures are applied to a backing film and the solvent is thereafter removed by drying.

For instance, DE 43 01 783 01 (LTS Lohmann) discloses a transdermal therapeutic system with galantamine as active ingredient, it being the transdermal therapeutic system, i.e., the active ingredient-containing patch, that delivers the galantamine to the skin. The system is equipped with a backing layer, which is impermeable to the active ingredient, and with a pressure-sensitively adhesive reservoir layer. With the known transdermal system there may be problems with residual solvents, since it is virtually impossible for the solvent to evaporate completely from the polymer matrix. Following its production, therefore, the system gives off solvent vapor for a long time, including on the skin and through the skin, during active ingredient delivery—and this is undesirable. As a result of the vapor given off, there are also fluctuations in the active ingredient concentration on application to the backing.

With temperature-sensitive active ingredients, the attempt to replace the polymer solution, which is supposed to act as a matrix for the release of the active ingredient, by a polymer melt will inevitably fail.

Also known are patch production methods in which backings are coated with pressure-sensitive adhesives. DE 197 55 437 C1 (Himmelsbach, Beiersdorf) discloses a method for the direct coating of an extensible, preferably textile backing material with a pressure-sensitive adhesive, in which the pressure-sensitive adhesive is applied through a cylindrical screen directly to the backing. The stress on the backing during application, however, leads easily to fluctuations in the layer thickness. Particularly in the case of thin layers, this would be a problem for drug patches, since the fluctuation in layer thickness would also entail a fluctuation in active ingredient concentration per application area. The only means to date of countering the problem of layer thickness fluctuations has been with layer thickness measurements carried out subsequently close to the product, in other words a quality control procedure, in which, possibly, it is necessary to accept a high reject fraction. Together with the layer thickness, however, the active ingredient concentration as well would fluctuate. For a therapeutic patch, subject to exacting requirements in terms of dosing accuracy (various pharmacopeias, and especially the U.S. Pharmacopeia), the aforesaid patches and methods are not contemplated, because they could result in metering inaccuracies that would be difficult to control in the production process.

SUMMARY

The object of the invention, therefore, was to provide a therapeutically useful patch and a method for producing it where the disadvantages in the prior art are avoided. The object further encompasses the idea that, in the patch, there should be at least one drug present with a high accuracy in terms of the declared dose, in order to allow this active ingredient to be delivered (evenly) from the patch and deployed topically or transdermally.

The object is achieved with a method for producing an active ingredient-containing polyurethane patch by reactive coating of a solvent-free, active ingredient-containing polyurethane composition, which is mixed immediately before or with the application procedure in a coating unit, onto an elastic and hence at the same time extensible backing film which has been made inelastic at least in the processing direction of the application, by means of an underlying, adhering, at least monoaxially inextensible auxiliary film.

The auxiliary film is not, for instance, a conveyor belt, since it has emerged that the detachment of the patch from the belt which is then inevitable as part of the process leads, in turn, to quality fluctuations that are difficult to monitor, if the patch composition is still too fresh. The solution provided by the invention is therefore that a separate auxiliary film is used which acts as a support for the elastic backing film to be coated, and which remains connected thereto until the polyaddition is virtually at an end (conversion of more than 95% in the urethane reaction), i.e., until a polymer end state is reached.

By "reactive coating" here is meant that all of the constituents envisioned for the polyurethane are mixed and immediately applied, so that the polyaddition reaction takes place during the coating operation and on the coated backing. One of the advantages of this method is that solvents can be completely avoided, since the polyurethane raw materials mixture is highly fluid and can be applied solvent-free in a thin layer to a backing. For this purpose, the reactive polyurethane composition brought together in the coating unit possesses a viscosity, preferably, in the range between 1000 and 5000 mPas.

In process-engineering terms it is beneficial that savings can be made on the line in terms of energy and heating sections. Another advantage is that no solvent can migrate and be delivered with the active ingredient to the patient and/or patch wearer. In environmental terms it is advantageous overall if the use of solvents is avoided, since no recycling problems are thrown up when the solvent dries or evaporates. A further advantage is that the adhesion of the fully reacted polyurethane to the elastic film which has been coated is particularly good if the polyurethane has been polymerized directly on the film. The adhesion is substantially better than if the elastic film were to be placed subsequently onto the fully polymerized polyurethane matrix. A bond between polyurethane and elastic film that is durable even under mechanical load can be produced much more easily by means of reactive coating.

Before the mixture for the reactive coating, that comprises all of the desired constituents, is prepared, all of these constituents are present separately or divided between at least two components which are unable, or able only very slowly, to react with one another and which are not brought together until immediately ahead of, or within, the coating unit. At least one polyurethane constituent, in that case preferably the isocyanate-reactive component, or at least one of the components which are brought together in the coating unit, comprises the active ingredient or ingredients. The active ingredient may be divided over a plurality of constituents. Where a polyol is used as isocyanate-reactive component, it is particularly preferred to mix the active ingredient or ingredients with said component.

The active ingredient or ingredients preferably comprise at least one active pharmaceutical or cosmetic ingredient for topical or transdermal administration that is liquid or solid at room temperature. It is also possible to use a mixture of two or more drugs, or additional, nonpharmaceutical, active ingredients are incorporated into the matrix in a mixture with one or more active pharmaceutical ingredients, examples of such additional ingredients being active skincare ingredients or other active cosmetic ingredients. An active ingredient means, in general, any substance which is intended to develop a particular activity—generally medical or cosmetic activity—on the skin (topically) or through the skin (transdermally).

The active ingredients that are used are a matter for decision by the skilled person. There are in principle no restrictions on the selection of active ingredients, apart from the fact that the active ingredient is to bind non-covalently and hence not in fixed location to the polyurethane matrix, and is not to alter its activity in contact with the polyurethane matrix. The skilled person is able to use preliminary tests to determine whether the active ingredient in question is suitable in this sense and to determine the kinetic with which the active ingredient is delivered from the matrix.

On the basis of their structure, alkaloids and steroids are suitable for delivery from a polyurethane matrix. It has been found in particular that the sex hormones, (including estrogens, more particularly estradiol, progestogens, progesterone, androgens, more particularly testosterone, including hormones/hormone derivatives synthesized identically or as analogs) can be delivered from the reactively coated polyurethane matrix. One active ingredient which is suitable, for example, is scopolamine.

The isocyanate-reactive component is composed preferably of polyols, which in turn comprise preferably polyester polyols and/or polyether polyols. The equivalent weight of the polyether polyols and/or polyester polyols is preferably greater than 300 (Mg(weight)>300).

Isocyanates used in the polyurethane composition are preferably aliphatic isocyanates, more preferably hexamethylene diisocyanate. The ratio of polyol to isocyanate is selected such that the polyol is present in excess, i.e., in one particularly preferred embodiment of the invention, the isocyanate index is less than 100, preferably less than 80. The fully reacted polyurethane then possesses inherent fluidity and is nevertheless dimensionally stable.

The fully reacted polyurethane is itself preferably pressure-sensitively adhesive, so that there is no need for an additional pressure-sensitive adhesive for attaching the patch. Such an adhesive could, however, be provided additionally on, for example, an overhanging liner layer, if this were to be desired in a specific case.

The pressure-sensitively adhesive polyurethane which is used as a matrix for the release of the active ingredient or ingredients contained therein adheres more effectively and above all more durably to the skin than do comparable, known pressure-sensitive adhesives for patches, based, for example, on PMMA, on styrene-butadiene copolymer or on silicone.

It is preferred, furthermore, if the fully reacted, active ingredient-containing, and solvent-free polyurethane and the elastic film are of water-vapor-permeable construction, preferably as water-vapor-permeable as possible with the base formulation, with extensive optimization of the likewise-required properties of pressure-sensitive tack, elasticity, conformability, and effective release of active ingredient. This ensures that the patch breathes and that occlusions of the skin, which can be disadvantageous, are avoided.

The elongation at break (measured in accordance with DIN EN ISO 1798 2008) of the fully reacted polyurethane is preferably >150%. This is advantageous in particular since it is known that elastic transdermal patches are more compatible, since they allow the skin to move in a natural way.

The polyurethane composition may where necessary comprise catalysts, chain extenders, initiators and/or crosslinkers and also further additives and auxiliaries that are customary in polyurethane chemistry. One particular advantage of the invention, however, is specifically that, to a large extent, auxiliaries and additives can be dispensed with. In general, the only additives and auxiliaries used should be those whose use on the skin can be considered benign. Possible auxiliaries are specified in WO 00/45797 A1, for example, and are hereby incorporated by reference. Preferred possible additives include organic and inorganic fillers, such as silica-based fillers, for example, aluminum oxide, carbomers; skincare agents and/or tackifiers, such as terpenes or terpene-containing resins, for example, more particularly tall resins or rosins.

The auxiliary film may be a release film. Generally suitable as auxiliary film is any inextensible film which merely attaches, i.e., does not permanently adhere, to the elastic film.

The elastic film to which the polyurethane coating is applied, and the inextensible auxiliary film, are to be able to be separated from one another, i.e., split, without mechanical damage to one of the films and preferably without any change in the individual films in respect of permanent elongation, visual alteration or alteration in properties of any kind whatsoever. The films placed against one another (elastic and inextensible film), or the films pressed against one another in an upstream method step, can preferably be split manually.

The method is preferably carried out continuously or semi-continuously with film webs, the film webs of elastic and inextensible film preferably having already been brought together beforehand—in an upstream method step on the same production line or as a delivered precursor product—to form a dual web, which is thereafter supplied to the coating unit.

In practice, the elastic backing film and the inextensible auxiliary film may be supplied to the coating unit separately, such as each from one roller, for example, and brought together—that is, placed on one another or pressed against one another—immediately ahead of the coating unit. Alternatively, in an upstream method step, the elastic film and the inextensible film may be placed on one another or pressed against one another and then wound up jointly. This loose, easily splittable assembly of two films may then be supplied, running from a roller, for example, to the coating unit. The films—elastic film and inextensible film—may also be used as a film assembly, in which case the assembly is separable with particular ease—i.e., preferably splittable by hand, as a result, for example, of dotwise adhesive lamination.

Each of the two films, the elastic and extensible film connected to the active ingredient layer from the polyurethane-backing matrix, and the inextensible, underlying (auxiliary) film, may per se be a multilayer film comprising coextruded or laminated plies.

The function of the inextensible film is to prevent any extension of the elastic film, which serves as a backing film for the active ingredient-containing polyurethane matrix and is to be durably connected to that matrix, during the coating operation, at least in processing direction, in order to prevent mechanical stress on the elastic film in the course of processing (primarily as a result of tensile forces) and hence to prevent layer thickness fluctuations and fluctuations in the concentration of active ingredient in the coating.

For as long as the inextensible film is joined to the elastic film, i.e., before the splitting of the films by hand by the plaster user or, where appropriate, before further processing steps, it makes the entire assembly, composed of elastic film and coating, inelastic and inextensible, at least in processing direction. For this purpose it is possible if desired to use an only monoaxially inextensible film which is inextensible in the processing direction, i.e., in the longitudinal direction of the film web, but is extensible transversely thereto, in the direction not exposed to tension. By an inextensible film, therefore, is meant here always a film which is inextensible "at least in processing direction", i.e., a film which is inextensible at least monoaxially in processing direction or, alternatively, isotropically.

"In processing direction" here means, in the case of a continuous method regime, in the direction of an advance of the film and/or material. If, for example, in the case of a discontinuous method regime, the active ingredient-containing polyurethane composition is spread in star formation over an area, so that there is no uniform processing direction present, there is also the possibility for no auxiliary film to be used that is only monoaxially inextensible. In this case, an isotropically inextensible film should be used.

The inextensibility of the assembly as a whole ensures that the dose of active ingredient per unit area remains constant. The inextensible film is therefore to remain connected to the elastic backing film during all processing steps which do or which could exert tension on the assembly. Where a liner film or release film is placed atop the polyurethane coating, this film too may preferably be inextensible. In that case the liner film may replace the inextensible auxiliary film, and the assembly remains inextensible overall for further processing steps.

One possible sequence of processing steps is therefore as follows: coating of the backing film which lies atop the auxiliary film—application of a liner film/release film to the coating—splitting of coated elastic backing film and inextensible auxiliary film, and removal of the auxiliary film—winding of the assembly: liner film-coating-backing film for an intermediate product in roll form (patch web), or direct further processing of the assembly to form individual patches.

Where no inextensible liner film or release film is to be placed atop the PU coating, the patch web, following removal of the auxiliary film, should no longer be exposed to tension, though diecutting to form individual patches remains a possibility.

As "inextensible" films it is possible to use commercially available films which are stated to be "inextensible". An "inextensible" film for the purposes of this invention is one which for lengthening by 10% requires a force of more than 3 newtons per cm of web width (>3 N/cm), preferably a force of more than 5 newtons per cm of web width (>5 N/cm). In the context of processing, during polyurethane application, the thickness of the auxiliary film is not an issue.

Inextensible films contemplated for the support film or auxiliary film include, in particular, the following: inextensible films of polyolefin, e.g., of polyethylene or polypropylene, of inextensible polyurethane, of polyester, polyamide or polycarbonate. The inextensible film may preferably have a nonstick coating or be plasma- or corona-treated.

As "elastic" films it is likewise possible to use commercially available films which are stated to be such. In principle, the elasticity of the elastic backing film is to correspond to the elasticity of the fully reacted matrix polyurethane, in other words to be greater than or equal thereto.

Elastic backing films contemplated include, in particular, the following: elastic PU films, other elastic polymer films, textile backings, and, generally, breathable patch outer materials, of the kind known to the skilled person. The elastic film is preferably 10 μm to 50 μm thick.

For the coating unit, there are a variety of configuration options. It is possible in principle to use all coating lines which allow a backing to be coated in a thin layer, in the millimeter range at most, with material of fluid viscosity.

In one preferred embodiment, the coating unit runs out into a slot and the active ingredient-containing, non-fully-reacted polyurethane composition is coated in a thin layer onto the elastic film. This can be done by running the film beneath the spatially fixed coating unit (particularly suitable application for continuous method regime) or by running a mobile coating unit over a fixed table carrying the film (application particularly suitable for discontinuous method regime).

In one alternative and likewise advantageous embodiment, the active ingredient-containing, non-fully-reacted polyurethane composition is applied with a metering and mixing machine and is spread with a coating blade (also referred to as a doctor blade) over the elastic film.

Another advantageous embodiment involves applying the active ingredient-containing, non-fully-reacted polyurethane composition with a metering and mixing machine and spreading it by pressure application of a roll.

A further preferred embodiment involves introducing the reacting mixture into a trough and causing it to emerge through holes/nozzles, in rakelike manner, from the trough at the bottom, or applying it to the elastic film through a large number of adjacently arranged nozzles, likewise in rakelike manner.

During the coating procedure, the films, or the assembly of films or coated films, are or is guided over or between rollers and preferably in sections over a table. Coating takes preferably on the table, at the beginning of the table or ahead of the table, on a preferably rigid roller.

In a development of the invention, an additional release film (liner film) may be placed onto the as yet not fully reacted polyurethane composition, and the composition may be spread between the films by a pressure application with a roll, the additional film preferably running from the roll.

Following full reaction of the polyurethane composition, and at the latest when the patch is in service, the release film is to be readily removable. For release films, there are numerous suitable materials available to the skilled person. In use for this purpose in the prior art, for example, are siliconized films and other nonstick films, including treated or coated release papers. These release films may also be used here. The release film at the same time forms a liner film for the PU coating and may likewise be inextensible in the sense of the invention as described above.

The coating, i.e., the layer of the solvent-free, active ingredient-containing polyurethane matrix which has formed following full reaction of the polyurethane composition on the elastic backing film, preferably possesses a layer thickness of less than or equal to 1000 μm. With further preference, coating takes place with a layer thickness of less than or equal to 500 μm, more particularly less than or equal to 300 μm, more preferably between 5 and 300 μm, even more preferably between 10 and 300 μm, and very preferably between 100 and 250 μm.

It is very preferred if within the reacting polyurethane a temperature of 79° C. is not exceeded, preferably 55° C. is not exceeded, and the temperature, more particularly, remains between room temperature and 50° C. throughout the method.

According to one preferred embodiment, furthermore, the elastic film and the inextensible film are split in a method step following completion of coating, and the inextensible film is removed from the coated elastic film. After this method step, the inextensible film, which is needed only for the coating operation and, where appropriate, as an application film, can be replaced by another patch liner—in other words, instead of the inextensible film removed, at least one further patch layer may applied. The further patch layers may comprise an additional patch adhesive, which may be applied at least to an overhanging marginal region of the additional layers. As the uppermost liner layer, a textile and/or skin-colored layer may be provided.

Particularly in the case of the continuous method regime on film webs, preferably, the coated film is cut, in a method step following completion of coating and full reaction of the polyurethane, and is thereby portioned to form patch sections, preferably including the underlying inextensible film or the further patch layer(s).

If, in the case of a narrow film web in patch width, the film web of the inextensible auxiliary film is selected to be wider than that of the elastic film with polyurethane matrix lying thereon, the inextensible film forms an overhang after the operation of cutting into patch sections with defined dosage. In this case, the inextensible film may be used as an application aid for application to the skin, with the overhang facilitating removal. The backing film and the auxiliary film in this case, i.e., the elastic film and the inextensible film, are split only at the application site of the patch, in other words on the skin of the patch wearer or patient.

For the achievement of the object, the invention further encompasses a polyurethane patch web, as processing stock or roll material, which is intended for portioning to form individual patches and which is notable for the presence of the following layers:
- a solvent-free layer of pressure-sensitively adhesive polyurethane, intended for direct skin contact, with a defined active ingredient concentration per unit area,
- an elastic backing film in surface contact with the aforesaid layer,
- an inextensible film in surface contact with the elastic backing film, or a patch liner film in surface contact with the elastic backing film, and/or an inextensible liner film or release film in contact with the layer of the pressure-sensitively adhesive polyurethane.

The patch liner film may be, as already described above, a customary, usually skin-colored patch liner material, e.g., an elastic textile material. In the case of this specific embodiment of the invention, the inextensible film, after conclusion of the application of PU, is replaced by the patch liner film.

Alternatively or additionally, the active ingredient-containing PU layer may be lined with a liner or release film. This film serves as a release film for the roll material and/or as a protective film for the active ingredient-containing PU. The liner or release film, which may be a siliconized or other nonstick film or a release paper, is removed either before conversion into patches, or, at the latest, by the user of the patch before application to the skin.

In a preferred embodiment, the patch liner film, where present, is coated with pressure-sensitive adhesive over its full area on the side facing the elastic film, and possesses a lateral overhang relative to the polyurethane patch web, i.e., relative to the polyurethane layer and to the elastic backing layer.

For the achievement of the object, the invention also encompasses a polyurethane patch for transdermal application of active ingredients, this patch being characterized by:
- a solvent-free layer of pressure-sensitively adhesive polyurethane, intended for direct skin contact, having a defined active ingredient concentration,
- an elastic backing film which lies directly on, and completely covers, the skin-remote side of the polyurethane layer,
- a liner film which completely covers and is in direct contact with the elastic film, and/or a liner film or release film which is in contact with the layer of pressure-sensitively adhesive PU and can be removed without residue from the PU layer.

The polyurethane patch of the invention may be cut or diecut into a shape desired for the patch from the patch web described above, which is formed as a direct method product in the case of a continuous method regime. The polyurethane patch is then an individual patch, formed by portioning of the patch web.

The liner consists either of the inextensible film or preferably, as already described above, of at least one further layer or film, with all of the further layers preferably being elastic. These further layers are applied after the inextensible auxiliary film has been removed from the base patch comprising elastic film and polyurethane matrix.

According to one alternative advantageous embodiment, the liner of the polyurethane patch is composed of an at least monoaxially inextensible film which can be split by hand from the elastic film. In this case, the inextensible film, which serves as a support for the coating procedure, does not need to be replaced.

The liner of the patch possesses or forms, preferably, an overhang which protects the base patch, comprising elastic film and polyurethane support—that is, the active ingredient-containing matrix—firmly connected to it. Where necessary, the patch can be gripped more easily by this overhang, and not only can be applied more effectively, without contacting the polyurethane layer, but also can be removed again from the skin later on.

In a development of the invention, on the solvent-free, active ingredient-containing layer of polyurethane, there is an additional release film, which can be removed without residue from the polyurethane layer.

The polyurethane layer of the patch, which forms the matrix for the delivery of the at least one active ingredient, is pressure-sensitively adhesive and conformable. The intimate contact that is necessary for the transition of the active ingredient from patch to the patch wearer, namely to and/or through the skin, can therefore be produced particularly effectively by means of the polyurethane delivery matrix (delivery system). The pressure-sensitive tack does away with the need for additional measures to affix the patch on the skin of the patch wearer.

Apart from topical active ingredients it is possible for active ingredients suitable in particular for transdermal application to be optimally deployed with the patch of the invention. By varying the layer thickness it is possible to adjust the delayed-release effect. The properties of the polyurethane with an isocyanate index of less than 100 allow the distribution and gradual outward migration of the active ingredient.

The production method ensures that the patch of the invention contains the active ingredient in a dose which deviates by less than ±5%, preferably ±1% or less, from the stated dose. This is a particular advantage, and actually renders the patch useful in the first place for many highly active therapeutic substances. In the case of fluctuations in the layer thickness, that might arise in the prior art through direct coating of an elastic film, the dose that is actually present in the individual patch cannot be stated with sufficient accuracy, and this, in many cases, is therapeutically untenable.

The conformability of the patch and the good, long-term adhesion guarantee intimate contact with the skin over the envisioned period of application of up to weeks or months.

DESCRIPTION OF THE DRAWINGS

The invention is elucidated in more detail below with reference to drawings, which are intended, however, to serve exclusively for nonlimiting illustration of the invention. In these drawings.

FIG. 3a—in cross section before removal of the auxiliary film,

FIG. 3b—in plan view,

FIG. 3c—in cross section without auxiliary film, with surrounding packaging;

DESCRIPTION

Figure 1:
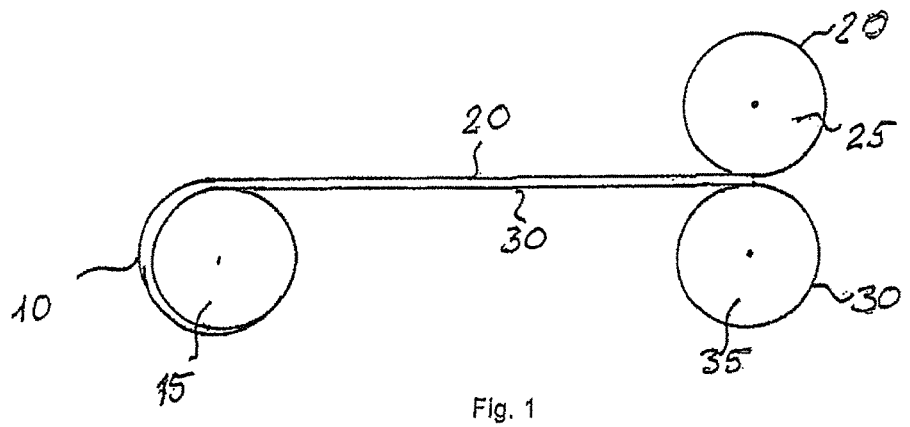
FIG. 1 shows the production of a dual web of backing film and auxiliary film in a simplified-diagrammatic cross-sectional representation.

FIG. 1 shows the production of a dual web 10 comprising an elastic backing film 20 and an inextensible auxiliary film 30. Both films, 20 and 30, are brought together in contra directional form, running from rollers 25 and 35. The dual web 10 formed by placing the films 20 and 30 together is rolled up onto a roller 15.

The static friction between the two films 20 and 30 is generally enough to cause the two films not to slip against one another during the subsequent coating of the dual web 10. In other exemplary embodiments, provision may be made for the films 20 and 30 to be laminated to one another, preferably dotwise, with pressure-sensitive adhesive. They are to continue to be able to be split by hand later on, i.e., separated from one another.

Figure 2:
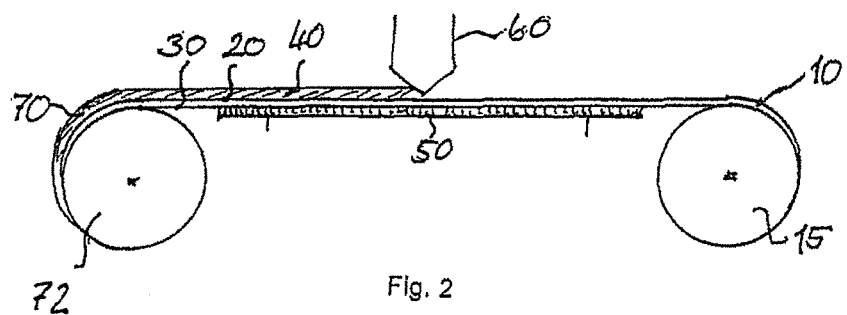
FIG. 2 shows the coating of the dual web with reacting PU composition in corresponding representation.

FIG. 2 shows diagrammatically, in cross section, how the dual web 10 obtained from FIG. 1 is coated with a polyurethane composition 40 containing active ingredient. The dual web 10 runs from the roller 15 and is led over a table 50 in such a way that the inextensible auxiliary film 30 glides over the table and at the same time serves as a reinforcing inextensible support for the elastic film 20. The elastic film 20 in turn forms a backing film for the still reactive polyurethane composition 40, which represents a matrix for an active ingredient contained therein, and which is applied with the aid of the coating unit 60, during the full reaction of the polyurethane composition, to the elastic backing film 20 of the dual web 10. The coating unit 60 is fed separately with the at least two components for the polyurethane reaction (not shown). When the coating operation is concluded and the polyurethane has largely fully reacted, the completed patch web 70 is wound onto a roller 72.

Figure 3:
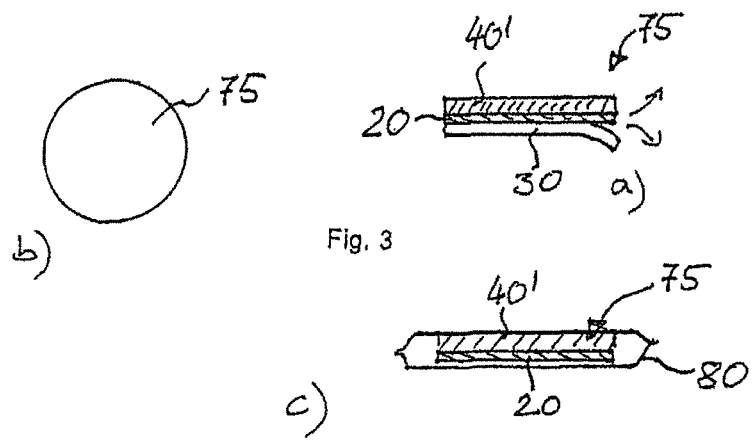
FIG. 3 shows a diecut patch.

FIG. 3 shows a patch 75, diecut circularly in this example from the patch web 70. FIG. 3a) shows the patch 75 in cross section with the layers of polyurethane composition 40' (containing active ingredient, fully reacted), elastic backing film 20, and inextensible auxiliary film 30. The films 20 and 30 are splittable, as indicated by the arrows in FIG. 3a).

FIG. 3b) shows the patch 75 in plan view. FIG. 3 c) shows the patch from FIGS. 3a) and 3b), after removal of the inextensible auxiliary film 30, in film or paper surround packaging 80. The polyurethane composition 40' is pressure-sensitively adhesive and attaches to the inside of the surround packaging 80, but can easily be removed from this packaging, an action which is to take place not until immediately prior to utilization of the patch. When the patch is applied to the skin of a user, the polyurethane composition 40' which contains the active ingredient is covered by the backing film 20. In contrast to what is shown in this example, there may also be a patch liner on the backing film. In that case the patch liner is composed either of the at least monoaxially inextensible auxiliary film 30 or of one or more films which replace the auxiliary film 30.

Of course, in a modification of the depiction shown in the example, a surround packaging may also contain more than one patch 75. For a plurality of patches 75, the surround packaging 80 may also be compartmentalized.

Figure 4:
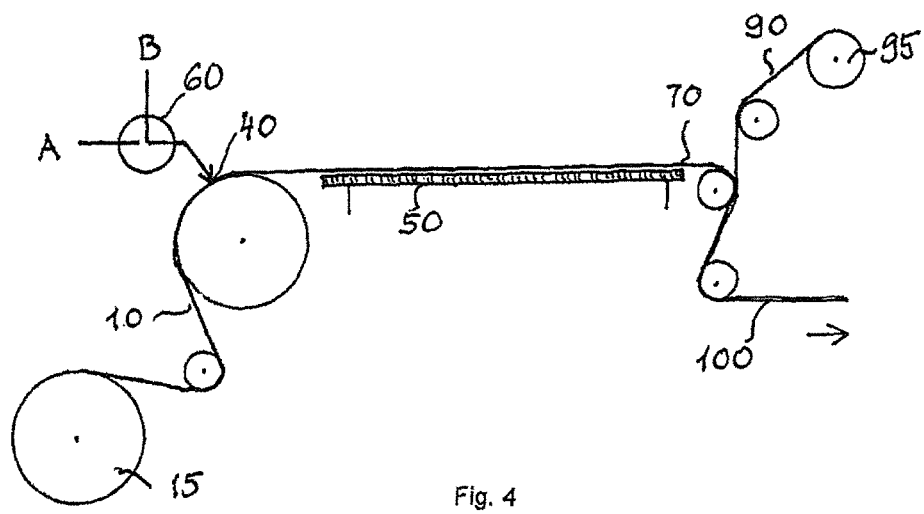
FIG. 4 shows a further exemplary embodiment of the coating of a dual web with subsequent application of a release and liner film.

FIG. 4 shows a further exemplary embodiment of the coating of a dual web of elastic backing film 20 and inextensible auxiliary film 30. The dual web 10 is guided, running off from a roller 15, over a rigid roller, to the table 50, and is coated on the rigid roller. In the coating unit 60, the polyurethane components A and B are brought together and applied. The fresh reactive polyurethane composition 40 reacts fully while it is being led over the table 50. After the table, the completed web 70, comprising dual film and coating, is brought together with a liner film 90 running from a roller 95. The product 100, comprising liner film 90 and coated dual web, is passed on in arrow direction for further processing and in this example is wound up into roll material, following removal of the inextensible film 30.

The properties of the patches obtained were tested as follows:

EXAMPLE 1

Transdermal Patch (TP) with Scopolamine

Production:

A mixture of polyol, containing 25 mg/g scopolamine, and polyisocyanate was applied by the method of the invention to a backing film 300 m thick. Circular transdermal patches (TP-1) with an area of 5 cm$^2$ were diecut from the film.

Similarly, TP with 2.5 mg scopolamine/g polyol were produced (TP-2).

Testing:

2 each of patches TP-1 and TP-2 were investigated on a comparative basis, relative to 2 each of standard commercial TP with scopolamine (TP-C: Scopoderm TTS, from Novartis, batch D613778, 3 mg scopolamine/5 cm$^2$) for release of active ingredient, as follows:

Method: "Paddle over disk method" (USP apparatus 5/PhEur 2.9.4.1)

Medium: Water with a temperature of 32° C.±1° C.

Stirring speed: 100 rpm

Analysis: HPLC

Figure 5:
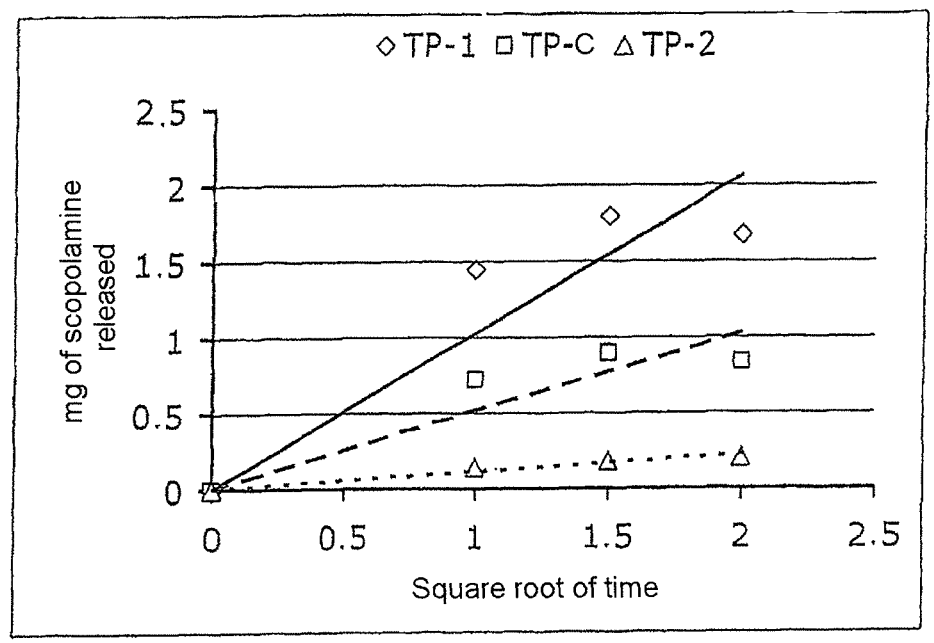
FIG. 5 shows a Higuchi plot for active ingredient release (scopolamine)

Results:

The tested patches release the scopolamine they contain in analogy to a root-t matrix diffusion mechanism (Higuchi plot, FIG. 5).

Discussion:

The measurement results correlate with the assumed root-t matrix diffusion mechanism (r>0.9). The slope of the regression line in the Higuchi plot (FIG. 5), which represents the rate of release of active ingredient, is 1.03 for TP-1,
0.52 for TP-C, and
0.11 for TP-2.

In the present example, the rate of active ingredient release from the TP of the invention can be controlled through the concentration of active ingredient in the patch.

The inventively produced patches with the higher concentration of active ingredient release scopolamine more rapidly than the comparison patch. The inventively produced patches with the low concentration of active ingredient release scopolamine more slowly than the comparison patch. It is therefore possible, by appropriate adaptation of the concentration of active ingredient, to set a release rate which is comparable with that of the comparison product.

EXAMPLE 2

Transdermal Patch (TP) with Testosterone

Production:

A mixture of polyol, with 5% testosterone, and polyisocyanate was applied by the method of the invention in different layer thicknesses(s) to a backing film. Circular transdermal patches with an area of 8.4 $cm^2$ were diecut from the film.

TP-100 (s=100 μm), TP-200 (s=200 μm), TP-300 (s=300 μm), TP-400 (s=400 μm)

Testing:

The patches TP-100 to TP-400 were tested in comparison with standard commercial TP with testosterone (Intrinsa: Intrinsa 300 μm/24 hours transdermal patch, Procter & Gamble Pharmaceuticals, 8.4 mg testosterone/28 $cm^2$, and also Testopatch: Testopatch Transdermal patch, 1.8 mg/24 h, 129 $cm^2$, Pierre Fabre Pharma GmbH, batch 7/04368/7) with regard to release of the active ingredient. In addition, investigation took place. In addition, circular sections with an area of 8.4 $cm^2$ were diecut from the standard commercial TP.

Method: "Paddle over disk method" (USP apparatus 5/PhEur 2.9.4.1)
Medium: Water with a temperature of 32° C.±1° C.
Stirring speed: 100 rpm
Analysis: HPLC Discussion:

The measurement results correlate initially with the assumed root-t matrix diffusion mechanism (r>0.9). When the active ingredient in the patches is exhausted, the correlation ends.

Figure 6:
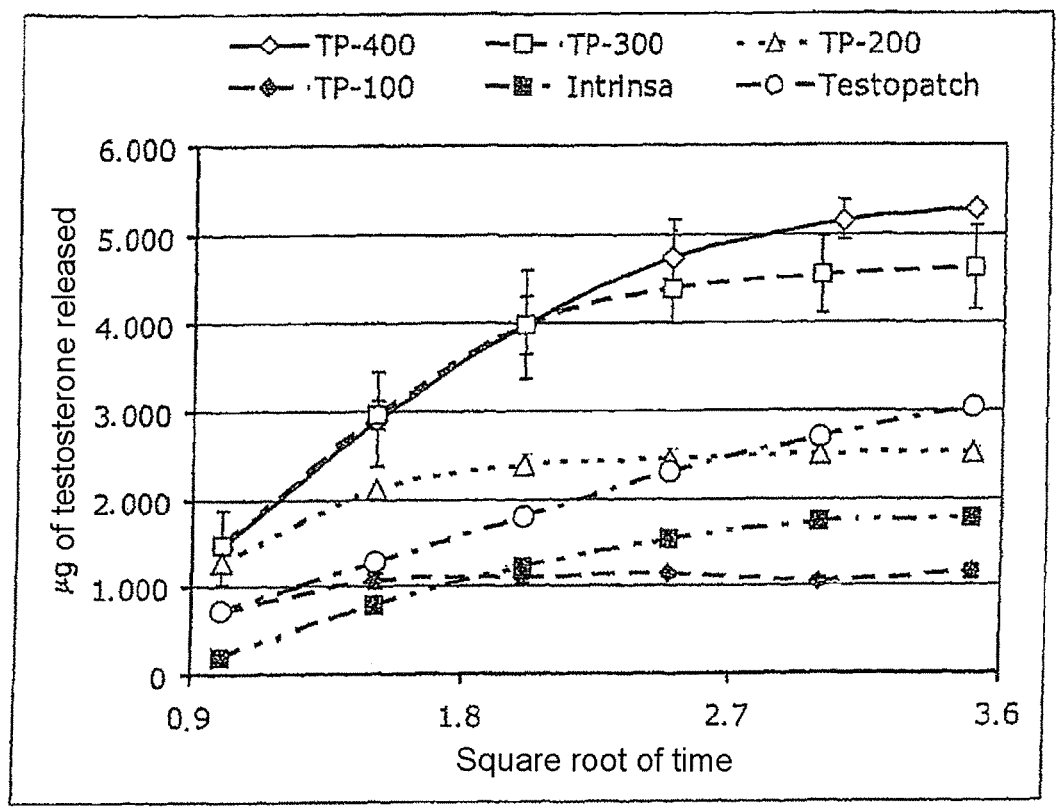
FIG. 6 shows a Higuchi plot for active ingredient release (testosterone)

The slope of the regression line in the Higuchi plot (FIG. 6), which represents the rate of release of active ingredient, is, for Testopatch, between the rate of release of the testosterone from the inventive patches with a layer thickness of 100 and 300 micrometers, and corresponds approximately to the rate of release in the case of the Intrinsa comparison product.

In the present example, the rate of active ingredient release from the TP of the invention can be controlled by the layer thickness applied to the backing film.

The inventively produced patches with the higher layer thickness release testosterone more quickly than do the comparison patches. The inventively produced patches with the low layer thickness release testosterone more slowly than do the comparison patches. It is therefore possible, for appropriate adaptation of the application layer thickness, to set a release rate which is comparable with that of the comparison products.

The invention claimed is:

1. A method for producing an active ingredient-containing polyurethane patch with a coating of a solvent-free, active ingredient-containing polyurethane composition on an elastic backing film, comprising the steps of:
    producing a dual web comprising said elastic backing film and at least one monoaxially inextensible auxiliary film, said at least monoaxially inextensible auxiliary film underlying and adhering to said elastic backing film thereby rendering said elastic backing film inextensible in at least a processing direction;
    feeding the dual web to a coating unit in the processing direction;
    reactive coating onto the elastic backing film of the dual web with the coating unit the solvent-free, active ingredient containing polyurethane composition, the solvent-free, active ingredient containing polyurethane composition being mixed before or with an application procedure of the coating unit, the reactive coating step producing a coated film on said dual web; and
    obtaining, from said dual web having said coated film, one or more individual patches containing at least a layer of said coated film and a layer of said elastic backing film.

2. The method of claim 1, wherein the method is carried out continuously or semicontinuously.

3. The method of claim 1, wherein the coating unit runs out into a slot, and the solvent-free active ingredient-containing polyurethane composition is supplied to the elastic film during said reactive coating step through said slot.

4. The method of claim 1, wherein the solvent-free, active ingredient containing polyurethane composition is applied at said coating unit with a metering mechanism and is spread with a coating blade on the elastic film.

5. The method of claim 1, wherein the solvent-free active ingredient-containing polyurethane composition is applied at said coating unit with a metering mechanism and is spread by pressure application of a roll on the elastic film.

6. The method of claim 1, wherein the reactive coating produces the coated film at a layer thickness less than or equal to 1000 μm.

7. The method of claim 1, wherein a temperature of 79° C. is not exceeded during said reactive coating.

8. The method of claim 1, further comprising the step of removing the at least monoaxially inextensible auxiliary film from the elastic film after the reactive coating step.

9. The method of claim 1 further comprising applying at least one further patch layer to said one or more individual patches.

10. The method of claim 1, wherein the obtaining step includes the step of cutting said coated film.

11. The method of claim 1 wherein said reactive coating step supplies said solvent-free, active ingredient containing polyurethane composition in a non-fully reacted state.

12. The method of claim 11 further comprising placing an additional release film onto the solvent-free, active ingredient containing polyurethane composition in said non-fully reacted state.

* * * * *